United States Patent
Kim et al.

(10) Patent No.: US 12,187,768 B2
(45) Date of Patent: *Jan. 7, 2025

(54) PROMOTER POLYNUCLEOTIDE, SIGNAL POLYPEPTIDE AND USE THEREOF

(71) Applicant: LIVEOME Inc., Suwon-si (KR)

(72) Inventors: Young In Kim, Seongnam-si (KR); Ji Yoon Song, Seongnam-si (KR); Ji Ae Yun, Suwon-si (KR); Seung Kee Cho, Suwon-si (KR); Hyeon Jin Noh, Suwon-si (KR)

(73) Assignee: LIVEOME INC., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,015

(22) Filed: Apr. 14, 2023

(65) Prior Publication Data

US 2023/0295249 A1 Sep. 21, 2023

Related U.S. Application Data

(62) Division of application No. 16/959,058, filed as application No. PCT/KR2018/013520 on Nov. 8, 2018, now Pat. No. 11,661,445.

(30) Foreign Application Priority Data

Dec. 29, 2017 (KR) ........................ 10-2017-0184819

(51) Int. Cl.
*C07K 14/335* (2006.01)
*C12N 15/74* (2006.01)

(52) U.S. Cl.
CPC ............ *C07K 14/335* (2013.01); *C12N 15/74* (2013.01); *C07K 2319/02* (2013.01)

(58) Field of Classification Search
CPC .............. C07K 14/335; C07K 2319/02; C12N 15/74
See application file for complete search history.

(56) References Cited

U.S. PATENT DOCUMENTS

| 8,759,088 | B2 | 6/2014 | Steidler et al. | |
| 11,661,445 | B2* | 5/2023 | Kim | C12N 15/746 |
| | | | | 435/69.1 |

FOREIGN PATENT DOCUMENTS

| JP | 2010515445 A | 5/2010 |
| JP | 2010517574 A | 5/2010 |
| WO | 2008084115 A2 | 7/2008 |
| WO | 2008103248 A1 | 8/2008 |
| WO | 2011039137 A1 | 4/2011 |

OTHER PUBLICATIONS

1st Office Action issued Aug. 8, 2023 of Japanese Patent Application No. 2022-137521.
1st Office Action issued Aug. 8, 2023 of Japanese Patent Application No. 2022-137522.
Database UniProtKB (online) Accession No. Q03D36 (https://rest.uniprot.org/unisave/Q03D36?format=txt&versions=55) Dec. 20, 2017 uploaded, Definition: Surface antigen.
Database UniProtKB online ,Accession No. K0MRM8 https://rest.uniprot.org/unisave/K0MRM8?format=txt&versions=23 Dec. 20, 2017 uploaded, Definition: Possible TrsG protein.
Database UniProtKB online ,Accession No. K6QSX2 https://rest.uniprot.org/unisave/K6QSX2?format=txt&versions=19 Dec. 20, 2017 uploaded, Definition: Putative peptidoglycan hydrolase.
Database UniProt [Online] May 27, 2015 (May 27, 2015), RecName: Full=Peptidase C51 domain-containing protein ECO:0000259-Prosite:PS50911}, XP55831074.
Djordjevic et al.; "Cloning of promoter-like sequences from *Lactobacillus paracasei* subsp. paracasei CG11 and their expression in *Escherichia coli*, Lactrococcus lactis, and Lactobacillus reuteri"; Can. J. Microbiol., vol. 40; 1994; pp. 1044-1050.
Extended European Search Report for EP Application 18897474.5 issued Aug. 20, 2021; 8 pages.
Rud, I. et al.; "A synthetic promoter library for constitutive gene expression in Lactobacillus plantarum"; Microbiology, vol. 152, part 4; 2006; pp. 1011-1019; DOI:10.1099/mic.0.28599-0.
JP Office Action issued Jul. 27, 2021 for JP Patent Application No. 2020-535620; 11 pages.
Zhang, W. et al.; "Complete Genome Sequence of Lactobacillus casei Zhang, a new Probiotic Strain Isolated from Traditional Homemade Koumiss in Inner Mongolia, China"; Journal of Bacteriology 192 (19); 5268-5269 (Year:2010).

* cited by examiner

*Primary Examiner* — Mary Maille Lyons
(74) *Attorney, Agent, or Firm* — CANTOR COLBURN LLP

(57) ABSTRACT

Provided are a promoter polynucleotide, a signal polypeptide and a polynucleotide encoding the signal polypeptide, and use thereof. A vector and a host cell each including the promoter polynucleotide and the polynucleotide encoding the signal polypeptide may efficiently express and/or extracellularly secrete a foreign protein.

17 Claims, 3 Drawing Sheets

Specification includes a Sequence Listing.

SEQUENCE LISTING

```
Sequence total quantity: 23
SEQ ID NO: 1            moltype = DNA  length = 31
FEATURE                 Location/Qualifiers
source                  1..31
                        mol_type = genomic DNA
                        organism = Lactobacillus paracasei
SEQUENCE: 1
tcgtcacggc gctgcttttt tcatacaaaa t                                   31

SEQ ID NO: 2            moltype = AA   length = 31
FEATURE                 Location/Qualifiers
```

```
                        source                  1..31
                                                mol_type = protein
                                                organism = Lactobacillus paracasei
SEQUENCE: 2
MKFNKVMITL VAAVTLAGSA SAVTPVFADT S                                         31

SEQ ID NO: 3            moltype = DNA   length = 93
        FEATURE                 Location/Qualifiers
        source                  1..93
                                mol_type = genomic DNA
                                organism = Lactobacillus paracasei
SEQUENCE: 3
atgaaattca ataaagtcat gatcacgttg gttgctgcag ttaccttagc aggttctgct         60
agcgccgtaa caccagtttt cgctgataca agc                                      93

SEQ ID NO: 4            moltype = DNA   length = 39
        FEATURE                 Location/Qualifiers
        source                  1..39
                                mol_type = other DNA
                                note = primer
                                organism = synthetic construct
SEQUENCE: 4
tctgcaggat atccgatcgt ccacaatcaa ggtgcttgg                                 39

SEQ ID NO: 5            moltype = DNA   length = 37
        FEATURE                 Location/Qualifiers
        source                  1..37
                                mol_type = other DNA
                                note = primer
                                organism = synthetic construct
SEQUENCE: 5
ttactggcag gtcgacgctt gtatcagcga aaactgg                                   37

SEQ ID NO: 6            moltype = DNA   length = 98
        FEATURE                 Location/Qualifiers
        source                  1..98
                                mol_type = other DNA
                                note = Cloning site
                                organism = synthetic construct
SEQUENCE: 6
aagcttctgc aggatatcgt cgacgcggcc gcagatctca tatggagctc cccgggggat         60
cctctagaac tagtgcatgc cgatcggcta gcctcgag                                  98

SEQ ID NO: 7            moltype = DNA   length = 1723
        FEATURE                 Location/Qualifiers
        source                  1..1723
                                mol_type = genomic DNA
                                organism = Leuconostoc mesenteroides
SEQUENCE: 7
tctgcttttt ggggtttgaa accgtcgttt tttcgacggt ttcttcttat cttgatacta         60
ttagaaacaa cgtcattttc aaaaagtgag gtaaaccctc gacacaactg ggtttaggcg        120
tattattgtg gtataaaata aatataaaaa aaacccacgt gagcttcgaa agtttgccga        180
cctcgaacgc gtgagttaat cttgtaaaaa tcgtatttgg atttactaga catagtttaa        240
agcttgaacc ctttgccgtc aagcttctg actgatttaa gtgaagcaag tacataacag        300
attaactctt ctcacgtggt tggtgagggg agtttttatt ttggctaatg aaaaagtctt        360
ggttgatcgg tcaaagtcag ggaaagttcg gccgtggcgg gagcgcaagt tggagaactt        420
gcagtatggt gactatttac aaatattgca ttataagaaa gctcatcgag ttaaagaatg        480
tggcgaagtt ttgcgttttg tggaagataa aaatggtcac aagaaattgg cgcagacttg        540
gttttgccat tctcgttttgt gtccgttatg taattggcgg cgggcaatga agcaatccaa        600
tcagttaaca cagattttga cggaagctgt taaacaacga aagacgggcc ggttcttatt        660
tttaacgttg acggttgaga atacaactgg tgatcaattg aagagtgagt tacgtcaaat        720
gggacgagct gttgcaaaaa ttttttcagta tacaaaagtt gccaaaaatt tattgggcta        780
tgtacgttcg actgaagtga ctgttaatca tgaagcgggt cagccaatgt accaccatca        840
tatgcatgtt ttgcttttttg tgaagaacca ttattttatg gggactgata actatatttc        900
acaagtagaa tggactggtt tttggcaacg ggcaatgaaa ttgacttatg taccaatggt        960
gaatgttgag gcagttaaac cgaatatgaa tcgccataaa aattcgttat ggctagtgc       1020
tcaagaaacg gctaaatatc aggtaaaatc taaagatatt ttgactaata atcaagaaca       1080
agacctacaa gtaattgatg atttggaacg agctttggct ggttcccggc aaattagcta       1140
tggcggtttg ctgaaagaaa ttcgcaagca gttgcaatta gaagacgttg agaatggtga       1200
tttgattaat acggatagtg atgatcaaaa ggttgaccaa gtggtacgcg agattgttgc       1260
taaatgggat tatcaaagaa aaaattattt tacattaaat gagttttgaa atctttaatg       1320
caaaataatt tttaggactt taatgtgcaa ataatttat gacacaatta ttttttgttt       1380
tgattctttt aatatttgac tttgtccctg gatacgccat tcattttttt ggggattccc       1440
aagaaggggt tgaattacta gataatataa tttcttttct gagttgtata attccacatt       1500
gtctattctt actgctaatg tttctgaata gtcaagttgt tttacttttt gttgtcttcc       1560
tgtttcttgc cactttggat ttgcttccat ttttaagatc tactccttt gttttttattt       1620
gtgtaactgt gttattata ctcttgttta gattcaatat ctgacgtttt tgcctcgcag       1680
agctcaaaact ttacgaagta aagtatattg ggctatacct tgc                        1723
```

```
SEQ ID NO: 8              moltype = DNA  length = 28
FEATURE                   Location/Qualifiers
source                    1..28
                          mol_type = other DNA
                          note = pLMT1-74rep- For
                          organism = synthetic construct
SEQUENCE: 8
aattgaattc tctgcttttt ggggtttg                                       28

SEQ ID NO: 9              moltype = DNA  length = 31
FEATURE                   Location/Qualifiers
source                    1..31
                          mol_type = other DNA
                          note = pLMT1-74rep- Rev
                          organism = synthetic construct
SEQUENCE: 9
aattgaattc gcaaggtata gcccaatata c                                   31

SEQ ID NO: 10             moltype = DNA  length = 2686
FEATURE                   Location/Qualifiers
source                    1..2686
                          mol_type = other DNA
                          note = pUC19 vector
                          organism = synthetic construct
SEQUENCE: 10
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt acccggggat   420
cctctagagt cgacctgcag gcatgcaagc ttggcgtaat catggtcata gctgtttcct   480
gtgtgaaatt gttatccgct cacaattcca cacaacatac gagccggaag cataaagtgt   540
aaagcctggg gtgcctaatg agtgagctaa ctcacattaa ttgcgttgcg ctcactgccc   600
gctttccagt cgggaaacct gtcgtgccag ctgcattaat gaatcggcca acgcgcgggg   660
agaggcggtt tgcgtattgg gcgctcttcc gcttcctcgc tcactgactc gctgcgctcg   720
gtcgttcggc tgcggcgagc ggtatcagct cactcaaagg cggtaatacg gttatccaca   780
gaatcagggg ataacgcagg aaagaacatg tgagcaaaag gccagcaaaa ggccaggaac   840
cgtaaaaagg ccgcgttgct ggcgtttttc cataggctcc gcccccctga cgagcatcac   900
aaaaatcgac gctcaagtca gaggtggcga acccgacag gactataaag ataccaggcg    960
tttccccctg gaagctccct cgtgcgctct cctgttccga ccctgccgct taccggatac   1020
ctgtccgcct ttctcccttc gggaagcgtg gcgctttctc atagctcacg ctgtaggtat   1080
ctcagttcgg tgtaggtcgt tcgctccaag ctgggctgtg tgcacgaacc ccccgttcag   1140
cccgaccgct gcgccttatc cggtaactat cgtcttgagt ccaacccggt aagacacgac   1200
ttatcgccac tggcagcagc cactggtaac aggattagca gagcgaggta tgtaggcggt   1260
gctacagagt tcttgaagtg gtggcctaac tacggctaca ctagaagaac agtatttggt   1320
atctgcgctc tgctgaagcc agttaccttc ggaaaaagag ttggtagctc ttgatccggc   1380
aaacaaacca ccgctggtag cggtggtttt tttgtttgca agcagcagat tacgcgcaga   1440
aaaaaaggat ctcaagaaga tcctttgatc ttttctacgg ggtctgacgc tcagtggaac   1500
gaaaactcac gttaagggat tttggtcatg agattatcaa aaaggatctt cacctagatc   1560
cttttaaatt aaaaatgaag ttttaaatca atctaaagta tatatgagta aacttggtct   1620
gacagttacc aatgcttaat cagtgaggca cctatctcag cgatctgtct atttcgttca   1680
tccatagttg cctgactccc cgtcgtgtag ataactacga tacgggaggg cttaccatct   1740
ggccccagtg ctgcaatgat accgcgagac ccacgctcac cggctccaga tttatcagca   1800
ataaaccagc cagccggaag ggccgagcgc agaagtggtc ctgcaacttt atccgcctcc   1860
atccagtcta ttaattgttg ccgggaagct agagtaagta gttcgccagt taatagtttg   1920
cgcaacgttg ttgccattgc tacaggcatc gtggtgtcac gctcgtcgtt tggtatggct   1980
tcattcagct ccggttccca acgatcaagg cgagttacat gatccccat gttgtgcaaa    2040
aaagcggtta gctccttcgg tcctccgatc gttgtcagaa gtaagttggc cgcagtgtta   2100
tcactcatgg ttatggcagc actgcataat tctcttactg tcatgccatc cgtaagatgc   2160
ttttctgtga ctggtgagta ctcaaccaag tcattctgag aatagtgtat gcggcgaccg   2220
agttgctctt gcccggcgtc aatacgggat aataccgcgc cacatagcag aactttaaaa   2280
gtgctcatca ttggaaaacg ttcttcgggg cgaaaactct caaggatctt accgctgttg   2340
agatccagtt cgatgtaacc cactcgtgca cccaactgat cttcagcatc ttttactttc   2400
accagcgttt ctgggtgagc aaaaacagga aggcaaaatg ccgcaaaaaa gggaataagg   2460
gcgacacgga aatgttgaat actcatactc ttcctttttc aatattattg aagcatttat   2520
cagggttatt gtctcatgag cggatacata tttgaatgta tttagaaaaa taaacaaata   2580
ggggttccgc gcacatttcc ccgaaaagtg ccacctgacg tctaagaaac cattattatc   2640
atgacattaa cctataaaaa taggcgtatc acgaggccct ttcgtc                  2686

SEQ ID NO: 11             moltype = DNA  length = 589
FEATURE                   Location/Qualifiers
source                    1..589
                          mol_type = genomic DNA
                          organism = Escherichia coli
SEQUENCE: 11
tttccatagg ctccgccccc ctgacagca tcacaaaaat cgacgctcaa gtcagaggtg     60
gcgaaacccg acaggactat aaagatacca ggcgtttccc cctggaagct ccctcgtgcg   120
```

```
ctctcctgtt ccgaccctgc cgcttaccgg atacctgtcc gccttttctcc cttcggaag    180
cgtggcgctt tctcatagct cacgctgtag gtatctcagt tcggtgtagg tcgttcgctc    240
caagctgggc tgtgtgcacg aaccccccgt tcagcccgac cgctgcgcct tatccggtaa    300
ctatcgtctt gagtccaacc cggtaagaca cgacttatcg ccactggcag cagccactgg    360
taacaggatt agcagagcga ggtatgtagg cggtgtgtaca gagttcttga agtggtggcc    420
taactacggc tacactagaa gaacagtatt tggtatctgc gctctgctga agccagttac    480
cttcggaaaa agagttggta gctcttgatc cggcaaacaa accaccgctg gtagcggtgg    540
ttttttttgtt tgcaagcagc agattacgcg cagaaaaaaa ggatctcaa              589

SEQ ID NO: 12           moltype = DNA   length = 471
FEATURE                 Location/Qualifiers
source                  1..471
                        mol_type = genomic DNA
                        organism = Mus musculus
SEQUENCE: 12
caatacagcc gagaggataa ctcttgcact cacttcccgg tgggccagag ccacatgttg     60
ttggaattaa gaacagcttt ctcacaggta aaaactttct tccaaacaaa ggatcagttg    120
gacaatattt tattgacaga ttcattgatg caagacttca aaggctattt ggggttgccag   180
gcgcttagcg aaatgataca gttctatctt gtcgaggtga tgccgcaggc agagaagcat    240
ggccctgaga taaagagca tttgaacagc ttgggagaaa aattgaaaac ccttcgtatg     300
agattacgac gttgtcatag attcttgccg tgcgagaaca agtcaaaggc tgtagagcaa    360
gtcaaaagcg actttaacaa attgcaggac caaggggtat acaaggcaat gaatgaattt    420
gacatcttta tcaactgcat agaggcgtac atgatgatta aatgaagag t              471

SEQ ID NO: 13           moltype = DNA   length = 18
FEATURE                 Location/Qualifiers
source                  1..18
                        mol_type = other DNA
                        note = primer
                        organism = synthetic construct
SEQUENCE: 13
ttttgacctc acccttaa                                                    18

SEQ ID NO: 14           moltype = DNA   length = 15
FEATURE                 Location/Qualifiers
source                  1..15
                        mol_type = other DNA
                        note = primer
                        organism = synthetic construct
SEQUENCE: 14
caatacagcc gagag                                                       15

SEQ ID NO: 15           moltype = DNA   length = 81
FEATURE                 Location/Qualifiers
source                  1..81
                        mol_type = genomic DNA
                        organism = Lactococcus lactis
SEQUENCE: 15
atgaaaaaaa agattatctc agctatttta atgtctacag tgatactttc tgctgcagcc     60
ccgttgtcag gtgtttacgc t                                                81

SEQ ID NO: 16           moltype = DNA   length = 30
FEATURE                 Location/Qualifiers
source                  1..30
                        mol_type = other DNA
                        note = primer
                        organism = synthetic construct
SEQUENCE: 16
gatacaagcg tcgaccaata cagccgagag                                       30

SEQ ID NO: 17           moltype = DNA   length = 30
FEATURE                 Location/Qualifiers
source                  1..30
                        mol_type = other DNA
                        note = primer
                        organism = synthetic construct
SEQUENCE: 17
ggaagcggag gtaccctcga gttatcaatg                                       30

SEQ ID NO: 18           moltype = DNA   length = 60
FEATURE                 Location/Qualifiers
source                  1..60
                        mol_type = other DNA
                        note = P11 promoter
                        organism = synthetic construct
SEQUENCE: 18
agatctagcg ctatagttgt tgacagaatg gacatactat gatatattgt tgctatagcg     60

SEQ ID NO: 19           moltype = DNA   length = 2774
```

```
FEATURE              Location/Qualifiers
source               1..2774
                     mol_type = genomic DNA
                     organism = Lactobacillus amylovorus
SEQUENCE: 19
gctagtgata cgacatcaac tgatcactca agcaatgata cagctgattc tgttagcgac   60
ggtgttattt tgcatgcatg gtgctggtcg ttcaacacga ttaaaaacaa cttgaaacag  120
attcatgacg ccggctacac agcggttcaa acttcacctg ttaatgaagt taaagttgga  180
aatagcgggt ctaagtcatt aaataactgg tattggctat atcagccaac taaatatagt  240
attggtaact attatttagg aacggaagct gaatttaagt caatgtgcgc tgctgctaaa  300
gaatataata tcaggatcat tgtcgatgca actctgaatg atacaacaag tgattatagt  360
gcaatttcgg atgaaattaa aagtatttca gattggacac atggtaacac acaaatttcg  420
aattggagtg atcgtgaaga tgttactcaa aattcgttgt taggtttcta tgattggaat  480
actcaaaatt ctcaagttca gacgtatttg aagaatcagt tgaacgctt gattctgac  540
ggagcttcag gcttccgtta tgatgcagct acgcatattg aacttccaag tcaatatgat  600
ggcagctatg gcagcaattt ctggccaaat attactgata tgggtctga atttcagtat  660
ggtgaagttt tgcaggactc gatttcaaaa gaatcagatt atgcaatta catgagtgtt  720
acagcttcaa attacggcaa tacgattcgc aatgcgttaa agaatcgtga ttttaccgca  780
agtactttgc agaatttcaa catcagtgtt ccagcttcta aattagtaac ttgggtcgaa  840
tcgcatgata attatgctaa cgatgatcaa gtttcgactt ggatgaatag tagtgatatt  900
aaattaggct gggctgttgt tgcttcgcgt tctggtagtg ttccgctgtt ctttgaccgt  960
ccagttgatg gtggtaatgg tactcggttc cctggcagtt cagaaattgg tgatgctggc 1020
agcagtttgt attatgataa agcagttgta gctgttaata aattccataa tgcaatggct 1080
ggtcaatctg aatatatttc taatccaaat ggcaatacca gatttttga aaatgaacgt 1140
ggcagcaaag gggttgtttt tgcaaacgct tccgacagtt catatagttt gaatgttaaa 1200
actagtttag ctgatgggac ttatgaaaac aaggctgatt cagatgaatt taccgttaaa 1260
aatggttatt taaccggtac aattcaagga cgtgaagttg ttgttcttta cggggatcca 1320
acaagcagca gcagtacaac aacagaaact aaaaaggttt attttgaaaa gccttcaagt 1380
tggggtagta gagtttatgc ctatgtttat aataaaaata cgaataaagc tataacttca 1440
gcttggcctg gcaaaaaaat gaccgcttta ggtaacgaca aatatgaatt ggatctcgac 1500
actgatgaag atgactctga tttagctgtt atctttaccg atgggacaaa gcaaacacca 1560
gcagctaatg aggctggttt tacctttacg gctgatgcca cttatgatca aaatggtgtc 1620
gtaaaaaagg tttattttga aaagccttca agttggggta gtagagtta tgcctatgtt 1680
tataataaaa atacgaataa agctataact tcagcttggc ctggcaaaaa aatgaccgct 1740
ttaggtaacg acaaatatga attggatctc gacactgatg aagatgactc tgatttagct 1800
gttatcttta ccgatgggac aaagcaaaca ccagcagcta atgaggctgg ttttaccttt 1860
acggctgatg ccacttatga tcaaaatggt gtcgtaaaaa aggtttattt tgaaaagcct 1920
tcaagttggg gtagtagagt ttatgcctat gtttataata aaaatacgaa taaagctata 1980
acttcagctt ggcctggcaa aaaaatgacc gctttaggta acgacaaata tgaattggat 2040
ctcgacactg atgaagatga ctctgattta gctgttatct ttaccgatgg gacaaagcaa 2100
acaccagcag ctaatgaggc tggttttacc tttacggctg atgccactta tgatcaaaat 2160
ggtgtcgtaa aaaaggttta ttttgaaaag ccttcaagtt ggggtagtag agtttatgcc 2220
tatgtttata taaaaatac gaataaagct ataacttcag cttggcctgg caaaaaaatg 2280
accgctttag gtaacgacaa atatgaattg gatctcgaca ctgatgaaga tgactctgat 2340
ttagctgtta tctttaccga tgggacaaag caaacaccag cagctaatga ggctggtttt 2400
acctttacgg ctgatgccac ttatgatcaa aatggtgtcg taaaaaaggt ttattttgaa 2460
aagccttcaa gttggggtag tagagtttat gcctatgtt ataataaaa tacgaataaa 2520
gctataactt cagcttggcc tggcaaaaaa atgaccgctt taggtaacga caaatatgaa 2580
ttggatctcg acactgatga agatgactct gatttagctg ttatctttac cgatgggaca 2640
aagcaaacac cagcagctaa tgaggctggt tttacccttta cggctgatgc cacttatgat 2700
caaaatggtg tcgtaagaac ttctgattca agcagcacat caagcaattc gtaagccgat 2760
accagcagtt catc                                                   2774

SEQ ID NO: 20        moltype = DNA  length = 20
FEATURE              Location/Qualifiers
source               1..20
                     mol_type = other DNA
                     note = primer
                     organism = synthetic construct
SEQUENCE: 20
aggcgcttag cgaaatgata                                               20

SEQ ID NO: 21        moltype = DNA  length = 20
FEATURE              Location/Qualifiers
source               1..20
                     mol_type = other DNA
                     note = primer
                     organism = synthetic construct
SEQUENCE: 21
ccttggtcct gcaatttgtt                                               20

SEQ ID NO: 22        moltype = DNA  length = 38
FEATURE              Location/Qualifiers
source               1..38
                     mol_type = other DNA
                     note = primer
                     organism = synthetic construct
SEQUENCE: 22
tgatacaagc gtcgacgcta gtgatacgac atcaactg                           38
```

```
SEQ ID NO: 23          moltype = DNA  length = 40
FEATURE                Location/Qualifiers
source                 1..40
                       mol_type = other DNA
                       note = primer
                       organism = synthetic construct
SEQUENCE: 23
cggaggtacc ctcgagttat caatggtgat ggtgatggtg                            40
```

PROMOTER POLYNUCLEOTIDE, SIGNAL POLYPEPTIDE AND USE THEREOF

CROSS REFERENCE TO RELATED APPLICATIONS

This application is a continuation of U.S. application Ser. No. 16/959,058, filed Sep. 16, 2021, which is a 371 National Stage filing of PCT/KR2018/013520, filed Nov. 8, 2018, which claims the benefit of priority to Korean Patent Publication No. 10-2017-0184819, filed Dec. 29, 2017.

SEQUENCE LISTING

The Instant Application contains a Sequence Listing which has been submitted electronically in XML format and is hereby incorporated by reference in its entirety. Said XML copy, created on Apr. 12, 2023 is named YPL2765USD and is 32,406 bytes in size.

TECHNICAL FIELD

Field

The present disclosure relates to a promoter polynucleotide, a signal polypeptide, and use thereof.

BACKGROUND ART

Microorganisms such as bacteria, yeast, and fungi are becoming increasingly important as hosts for recombinant expression.

Bacteria such as *Lactobacillus* or *Streptococcus* sp. may be useful as delivery vehicles. In addition, generally recognized as safe (GRAS) microorganisms may be administered to humans or animals.

To achieve a high expression level of a foreign product in lactic acid bacteria, there is a demand for novel promoter and signal polypeptides that may be isolated from lactic acid bacteria and may express and secrete the foreign product, in particular a protein, at a high level.

DISCLOSURE OF INVENTION

Technical Problem

An aspect provides an isolated promoter.

Another aspect provides a recombinant polynucleotide including the promoter.

Still another aspect provides a host cell including the recombinant polynucleotide.

Still another aspect provides a method of producing a product using the host cell.

Still another aspect provides an isolated signal polypeptide and a polynucleotide encoding the same.

Still another aspect provides a recombinant polynucleotide including the polynucleotide encoding the isolated signal polypeptide.

Still another aspect provides a host cell including the recombinant polynucleotide encoding the isolated signal polypeptide.

Still another aspect provides a method of producing a protein using the host cell including the recombinant polynucleotide encoding the isolated signal polypeptide.

Solution to Problem

An aspect provides an isolated promoter including a polynucleotide having a sequence identity of 85% or more with a nucleotide sequence of SEQ ID NO: 1 (hereinafter, referred to as 'PR4 promoter').

Another aspect provides a recombinant polynucleotide including the promoter. As used herein, the term "promoter" refers to a nucleic acid molecule, particularly, a region on a DNA molecule, to which an RNA polymerase binds to initiate transcription. The promoter is generally located upstream, i.e., 5' of a sequence to be transcribed, which is regulated by the promoter. The promoter may be a constitutive promoter. The promoter may have a sequence identity of 80% or higher, 85% or higher, 90% or higher, 95% or higher, 96% or higher, 97% or higher, 98% or higher, 99% or higher, or 100% with the nucleotide sequence of SEQ ID NO: 1. The promoter may have the nucleotide sequence of SEQ ID NO: 1.

The recombinant polynucleotide may be a vector. As used herein, the term "vector" refers to a nucleic acid molecule capable of propagate another nucleic acid linked thereto. The vector may include a vector as a self-replicating nucleic acid structure as well as a vector incorporated into the genome of a host cell into which it has been introduced. An expression vector refers to a vector that directs expression of a nucleic acid operably linked thereto. The vector may be a plasmid or a vector derived from a virus.

The vector may be a cloning vector or an expression vector. The expression vector may include a nucleotide sequence encoding a protein, the nucleotide sequence being operably linked to the promoter.

The expression vector may include the promoter, and a first polynucleotide including a nucleotide sequence encoding a product, the first polynucleotide being operably linked to the promoter. The product may include any product which may be produced by expression of the first polynucleotide. The product may be a polypeptide or a nucleic acid. The polypeptide may be a cytokine such as IL-10 or an enzyme such as amylase. The nucleic acid may be DNA or RNA.

As used herein, the term "operably linked" means a linkage that allows transcription or translation to produce a functional transcription or translation product.

The vector may further include one or more selected from the group consisting of a ribosome binding site (RBS), a cloning site, a selection marker gene, a transcription terminator, and a translation initiator factor. The cloning site may be operably linked to the promoter. The cloning site may be a multiple cloning site.

The recombinant polynucleotide may be a recombinant polynucleotide wherein a second polynucleotide encoding a signal polypeptide including an amino acid sequence having a sequence identity of 85% or more with an amino acid sequence of SEQ ID NO: 2 (hereinafter, referred to as "SP4 signal polypeptide") is operably linked between the promoter and the first polynucleotide. In this case, the first polynucleotide may encode a polypeptide.

As used herein, the term "signal polypeptide" refers to a sequence that is present at the N-terminus of a secreted protein precursor but not present in a naturally existing mature protein. The signal polypeptide may be cleaved off from the protein precursor. In general, the signal polypeptide may be cleaved by a protease when extracellularly secreted. The protease may be generally called signal peptidase. The signal polypeptide may have a sequence identity of 80% or more, 85% or more, 90% or more, 95% or more, 96% or more, 97% or more, 98% or more, 99% or more, or 100% with the amino acid sequence of SEQ ID NO: 2. The signal polypeptide has activity to allow extracellular secretion of an expression product of a gene which is fused in frame to the nucleotide sequence encoding the signal polypeptide.

As used herein, the term "secretion" of a protein or a polypeptide molecule may include transport of the protein or the polypeptide molecule outside of a bacterial cell, presence of the protein or the polypeptide molecule in a completely free form in a medium, presence of only part of the protein or the polypeptide molecule outside the bacterial cell, and presence of the protein or the polypeptide molecule on the surface of the bacterial cell.

The signal polypeptide may be derived from *L. paracasei* and may have a secretion-promoting ability. The second polynucleotide may have a nucleotide sequence of SEQ ID NO: 3.

Another aspect provides a host cell including the recombinant polynucleotide. The host cell may be a bacterial cell. The bacterial cell may be a Gram-positive bacterium. The bacterial cell may be a lactic acid bacterium or may belong to the genus *Escherichia*. The lactic acid bacterium may be the genus *Lactobacillus, Lactococcus, Bifidobacteria, Streptococcus, Leuconostoc, Weissella, Pediococcus*, or *Enterococcus*.

The recombinant polynucleotide may be introduced into the host cell by a common nucleic acid introduction method. The nucleic acid introduction method may include electroporation, transformation, transduction, or transfection.

Still another aspect provides a method of producing a product or a metabolite thereof, the method including producing the product by culturing the host cell in a medium; and isolating the product or the metabolite thereof from the culture. The product may include any product that may be produced by expression of the first polynucleotide. The product may be a polypeptide or a nucleic acid. The polypeptide may be a cytokine such as IL-10 or an enzyme such as amylase. The nucleic acid may be DNA or RNA. The metabolite may be a substance produced when the product exerts its activity in a cell. For example, when the product is an enzyme, the metabolite may be a direct product produced when the enzyme exerts its enzymatic activity, or a substance produced from a metabolic pathway in which the enzyme is involved.

In the method, the culturing may be performed by a common method known in the art according to a host cell selected. The medium used in the culturing may include, as a sugar source, for example, carbohydrate e.g., glucose, saccharose, lactose, fructose, maltose, and starch, oil and fat. e.g., soybean oil, sunflower oil, castor oil, coconut oil, etc., a fatty acid, e.g., palmitic acid, stearic acid, and linolenic acid, glycerol, and an organic acid, e.g., acetic acid, singly or in a mixture. The medium may include, as a nitrogen source, for example, peptone, a yeast extract, a meat extract, a malt extract, corn steep liquor, soy meal, urea, or an inorganic compound, e.g., ammonium sulfate, ammonium chloride, ammonium phosphate, ammonium carbonate, or ammonium nitrate, singly or in a mixture. The medium may include, as a phosphorous source, for example, potassium dihydrogen phosphate, dipotassium hydrogen phosphate, or a corresponding sodium-containing salt thereof. The medium may include, for example, a metal salt, e.g., magnesium sulfate or iron sulfate, which is required for growth. Also, in the culturing, substances required for growth, such as amino acids and vitamins, or suitable precursors may be added to the culture. Those components may be added to the culture in a proper manner, for example, in a batch or continuous manner during the culturing.

The culturing may be performed under aerobic conditions, microaerobic, unaerobic conditions, or a combination thereof.

The method may further include isolating the product from the culture. The isolating may be performed by an appropriate method according to a kind of a product to be selected. When the product is a protein, the isolating may include isolating the protein from a supernatant after removing cells by centrifugation of the culture, or isolating the protein by cell disruption after recovering the cells. The isolating may be subjected to one or more processes of salting-out, precipitation, chromatography, centrifugation, and filtration. The chromatography may be one or more of anion exchange chromatography, cation exchange chromatography, size exclusion chromatography, and affinity chromatography.

Still another aspect provides an isolated signal polypeptide including an amino acid sequence having sequence identity of 85% or more with the amino acid sequence of SEQ ID NO: 2. The signal polypeptide may have sequence identity of 80% or more, 85% or more, 90% or more, 95% or more, 96% or more, 97% or more, 98% or more, 99% or more, or 100% with the amino acid sequence of SEQ ID NO: 2.

Still another aspect provides a polynucleotide encoding the signal polypeptide. The polynucleotide encoding the signal polypeptide may have a nucleotide of SEQ ID NO: 3.

Still another aspect provides an expression vector including the second polynucleotide encoding the signal polypeptide and the first polynucleotide encoding the protein, wherein the second polynucleotide is operably linked to the promoter and the first polynucleotide is fused in frame to the second polynucleotide.

Still another aspect provides a host cell including the expression vector. The host cell may be a bacterial cell. The bacterial cell may be a Gram-positive bacterium. The bacterial cell may be a lactic acid bacterium or may belong to the genus *Escherichia*. The lactic acid bacterium may be the genus *Lactobacillus, Lactococcus, Bifidobacteria, Streptococcus, Leuconostoc, Weissella, Pediococcus*, or *Enterococcus*.

The recombinant polynucleotide may be introduced into the host cell by a common nucleic acid introduction method. The nucleic acid introduction method may include electroporation, transformation, transduction, or transfection.

Still another aspect provides a method of producing a protein, the method including producing the protein by culturing the host cell in a medium; and isolating the protein from the culture.

In the method, the culturing may be performed by a common method known in the art according to a host cell to be selected. The medium used in the culturing may include, as a sugar source, for example, carbohydrate e.g., glucose, saccharose, lactose, fructose, maltose, and starch, oil and fat, e.g., soybean oil, sunflower oil, castor oil, coconut oil, etc., a fatty acid, e.g., palmitic acid, stearic acid, and linolenic acid, glycerol, and an organic acid, e.g., acetic acid, singly or in a mixture. The medium may include, as a nitrogen source, for example, peptone, a yeast extract, a meat extract, a malt extract, corn steep liquor, soy meal, urea, or an inorganic compound, e.g., ammonium sulfate, ammonium chloride, ammonium phosphate, ammonium carbonate, or ammonium nitrate, singly or in a mixture. The medium may include, as a phosphorous source, for example, potassium dihydrogen phosphate, dipotassium hydrogen phosphate, or a corresponding sodium-containing salt thereof. The medium may include, for example, a metal salt, e.g., magnesium sulfate or iron sulfate, which is required for growth. Also, in the culturing, substances required for growth, such as amino acids and vitamins, or suitable precursors may be added to the culture. Those components may be added to the culture in a proper manner, for example, in a batch or continuous manner during the culturing.

The culturing may be performed under aerobic conditions, micro aerobic conditions, unaerobic conditions, or a combination thereof.

The method may further include isolating the protein from the culture. The isolating may include isolating the protein from a supernatant after removing cells by centrifugation of the culture, or isolating the protein by cell disruption after recovering the cells. The isolating may be subjected to one or more processes of salting-out, precipitation, chromatography, centrifugation, and filtration. The chromatography may be one or more of anion exchange chromatography, cation exchange chromatography, size exclusion chromatography, and affinity chromatography.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Advantageous Effects of Invention

An isolated promoter and a recombinant polynucleotide including the same according to an aspect may be used in efficiently expressing a foreign gene.

A host cell including the recombinant polynucleotide according to another aspect may be used in efficiently expressing a foreign gene.

A method of producing a product using the host cell according to still another aspect may be used to efficiently produce the product.

An isolated signal polypeptide, a polynucleotide encoding the signal polypeptide, and a recombinant polynucleotide including the polynucleotide according to still another aspect may be used in extracellularly secreting a foreign protein.

A host cell including the recombinant polynucleotide including the polynucleotide encoding the isolated signal polypeptide according to still another aspect may efficiently secrete a product of a foreign gene out of the cell.

A method of producing a protein using the host cell according to still another aspect may be used to efficiently produce the protein.

BRIEF DESCRIPTION OF DRAWINGS

These and/or other aspects will become apparent and more readily appreciated from the following description of the embodiments, taken in conjunction with the accompanying drawings in which.

BEST MODE FOR CARRYING OUT THE INVENTION

Hereinafter, the present disclosure will be described in more detail with reference to Examples. However, these Examples are for illustrative purposes only, and the scope of the present disclosure is not intended to be limited by these Examples.

Example 1: Cloning of Promoter and Signal Polypeptide and Examination of Effects Thereof 1. Cloning of Promoter and Signal Polypeptide A promoter and a nucleotide sequence encoding a signal polypeptide were amplified by PCR. In detail, PCR was performed using a genome of *Lactobacillus paracasei* LMT1-21 (Accession No: KCTC 13422BP) as a template and primers to obtain an amplification product of 593 kb. The used primers were PS4_F/R (SEQ ID NOS: 4 and 5).

The amplification product was ligated to pMT54 vector which had been digested with EcoRV and Sal1 by Infusion cloning (Clontech). Thereafter, the vector was transformed into *E. coli* Top 10 strain (Invitrogen) by a method of Sambrook et al. (Sambrook et al. Molecular cloning: A laboratory Manual, 2nd edition, 1989). Thereafter, the transformed *E. coli* was spread on an LB plate supplemented with 10 μg/ml chloramphenicol to obtain colonies. The pMT54 vector was recovered from the obtained colonies, followed by sequencing analysis. As a result, the vector was confirmed to include a PR4 (SEQ ID NO: 1)-SP4-encoding nucleotide sequence (SEQ ID NO: 3). Hereinafter, this vector is referred to as a pMT54-PR4-SP4 vector.

The pMT54 vector was a vector in which a multiple cloning site (SEQ ID NO: 6) was introduced into HindIII and XhoI restriction sites of pMT48 vector. The multiple cloning site has multiple restriction enzyme recognition sites and is tagged with human influenza hemagglutinin (HA) to confirm expression of a target protein. The pMT48 vector was a vector in which Rep gene (SEQ ID NO: 7) which is an origin of replication of a plasmid pLMT1-74 was introduced into the EcoRI site of pUC19 (New England Biolabs). The pMT48 vector was constructed as follows.

First, a tentative plasmid pLMT1-74 was isolated from a LMT1-74 strain (*Leuconostoc mesenteroides* KCTC 13164BP) which had been isolated from kimchi using a plasmid midi kit (Qiagen, Inc., Valencia, CA). PCR was performed using the plasmid pLMT1-74 as a template and oligonucleotides of SEQ ID NOS: 8 and 9 as primers to amplify Rep gene (SEQ ID NO: 7) which is an origin of replication of plasmid pLMT1-74. The amplified product was digested with EcoRI, and ligated to pUC19 which had been digested with the same enzyme to obtain the pMT48 vector. The polynucleotide of SEQ ID NO: 7 may be also chemically synthesized. The vector pUC19 has a nucleotide sequence of SEQ ID NO: 10.

Figure 1:
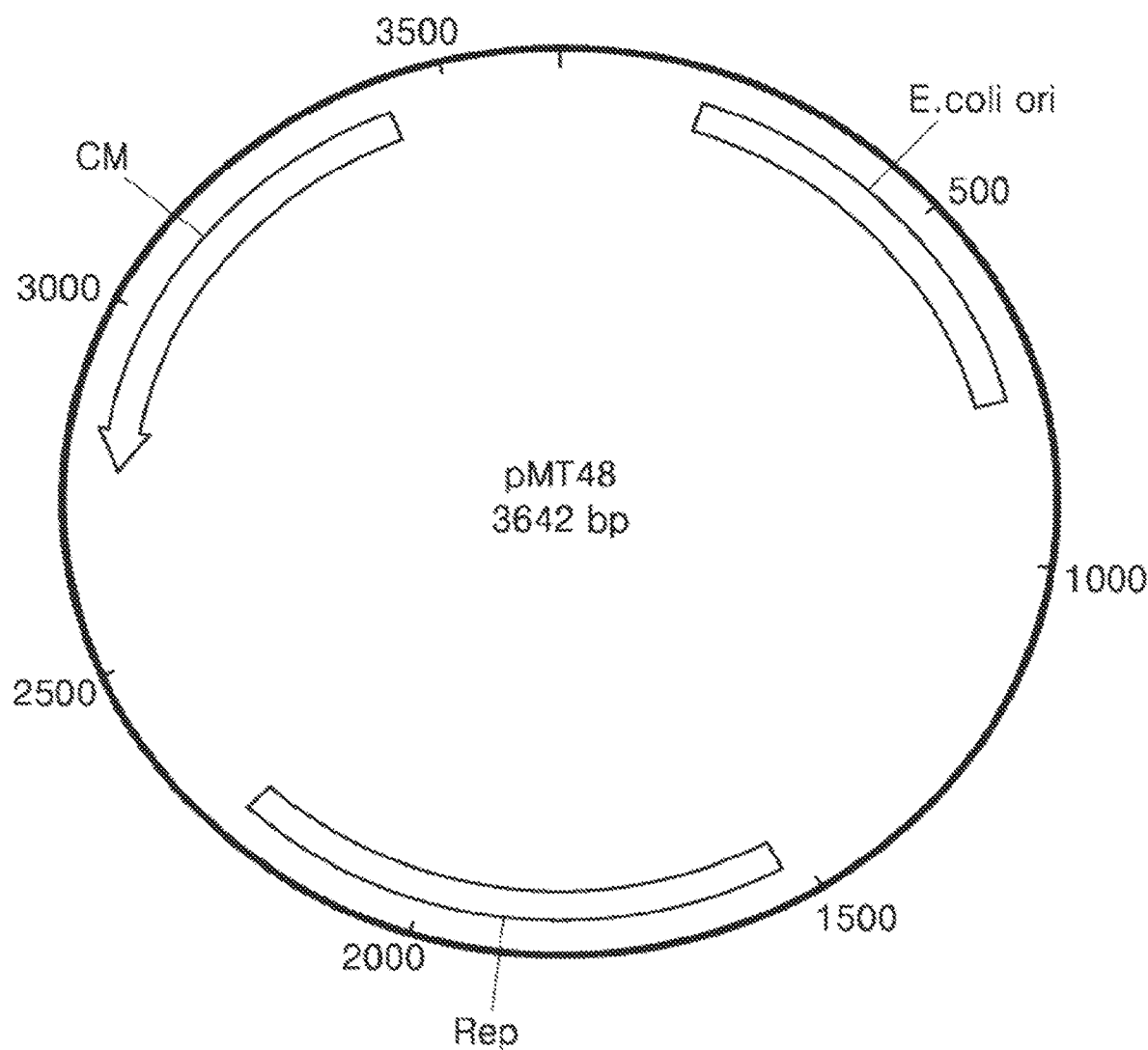
FIG. 1 illustrates the construction of a shuttle vector pMT48 between *E. coli* and lactic acid bacteria.

FIG. 1 illustrates the composition of a shuttle vector pMT48 between *E. coli* and lactic acid bacteria. In this vector, Rep has the nucleotide sequence of SEQ ID NO: 7 and is a partial sequence of Rep origin which is an origin of replication of a universal lactic acid bacterial host-vector pLMT1-74, and provides a replication ability for lactic acid bacteria. *E. coli* ori represents an origin of DNA replication of *E. coli*, and has pUC19 ori, i.e., a nucleotide sequence of SEQ ID NO: 11. CM represents a chloramphenicol resistance gene encoding chloramphenicol acetyltransferase.

2. Cloning of Target Protein IL-10

(1) Construction of Experimental Vector: pMT54-PR4-IL10-SP4 Vector

Figure 2:
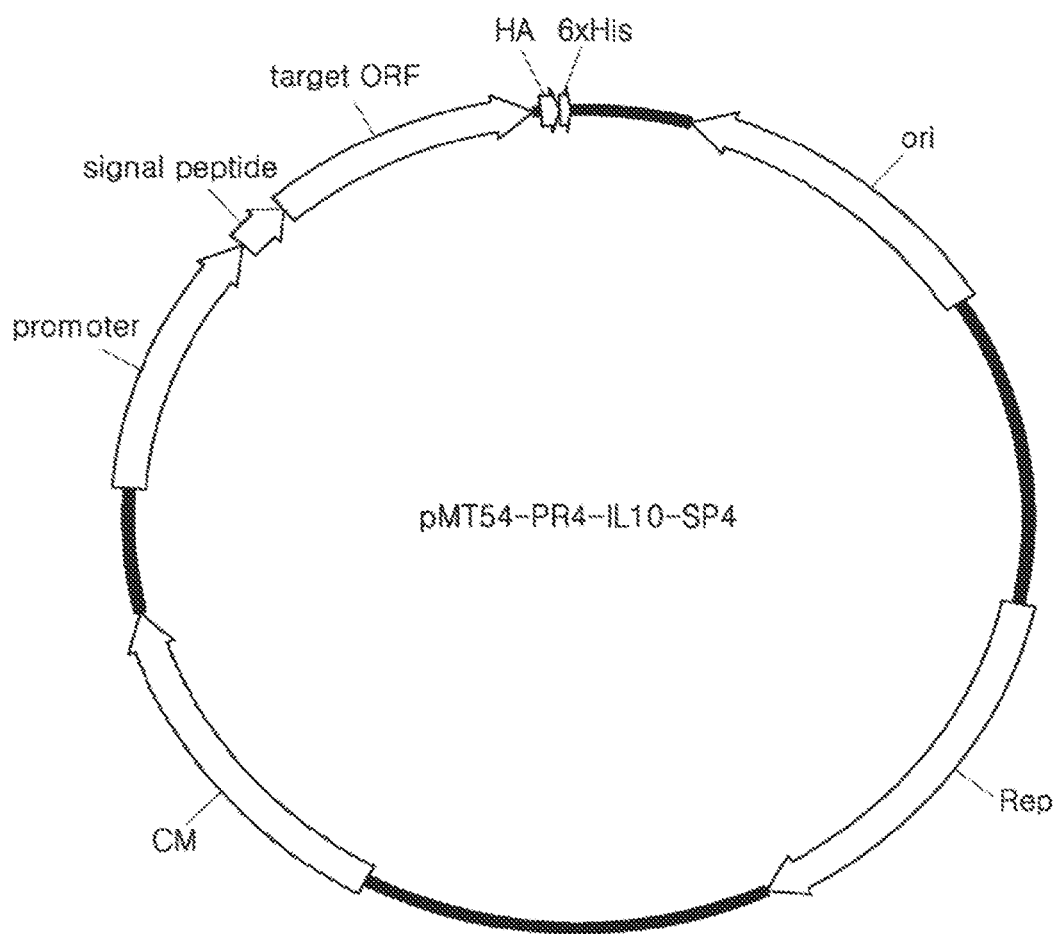
FIG. 2 illustrates the construction of a pMT54-PR4-IL10-SP4 vector.

Synthesis of IL-10 gene (SEQ ID NO: 12) was conducted by Macrogen Inc. (Korea). The synthesized gene fragment and the pMT54-PR4-SP4 vector were treated with restriction enzymes SalI and XhoI to cleave cloning sites of the vector. The cleaved product was purified using a Gel purification kit (Bioneer), and dephosphorylated using alkaline phosphatase. To a mixture of 1 µl of the prepared vector DNA, 3 µl of the gene (IL-10), 0.5 µl of T4 DNA ligase (Takara), and 1 µl of buffer, 5.5 µl of distilled water was added to prepare total 10 µd of a reaction mix. This reaction mix was incubated at 16° C. for 12 hours to ligate the gene into the cloning site of the vector. The obtained ligation product was transformed into *E. coli* Top 10 strain in the same manner as above, followed by sequencing. As a result, introduction of the gene was confirmed, and this product was designated as a pMT54-PR4-IL10-SP4 vector. FIG. 2 illustrates the composition of the pMT54-PR4-IL10-SP4 vector. In FIG. 2, promoter, signal peptide, and target gene represent PR4, SP4, and IL-10, respectively. The vector, which is a shuttle vector between *E. coli* and lactic acid bacteria, includes an origin of replication of *E. coli* (origin), an origin of replication of lactic acid bacteria (rep gene), and a chloramphenicol resistance gene. The promoter, signal peptide, target gene, HA tag, and His are linked at the multiple cloning site.

(2) Construction of Control Vector 1: pMT54-PR4-IL10-USP45 Vector

A vector was constructed in the same manner as in the experimental vector, except that the polynucleotide SP4 encoding the signal polypeptide was replaced by USP45 polynucleotide. This is to examine an effect of a different signal polypeptide on extracellular secretion of IL-10 protein when the same promoter was used.

In detail, PCR was performed using the pMT54-PR4-IL10-SP4 vector as a template and oligonucleotides of SEQ ID NOS: 13 and 14 as primers to amplify the vector from which SP4 was excluded. A USP45-encoding polynucleotide (SEQ ID NO: 15) was synthesized (Macrogen, Korea). The amplified product and the USP45-encoding polynucleotide were ligated by an infusion cloning method, and introduced into *E. coli* to clone a pMT54-PR4-IL10-USP45 vector. USP45 is a signal polypeptide derived from *Lactococcus lactis* and is known to play a role in secreting protein products such as homologous proteinase (PrtP) and *Bacillus stearothermophilus*-derived alpha-amylase (van Asseldonk M1, et al. Mol Gen Genet. 1993 September; 240(3):428-34).

(3) Construction of Control Vector 2: pMT54-P11-IL10-SP4 Vector

A vector was constructed in the same manner as in the experimental vector, except that the promoter PR4 was replaced by P11 promoter. This is to examine an effect of a different promoter on expression of IL-10 protein when the same signal polypeptide was used. P11 is a synthetic promoter having a strong transcription initiation activity in *Lactobacillus plantarum* (Lars Axelsson, Microbiology (2006), 152, 1011-019).

In detail, PCR was performed using the pMT54-PR4-IL10-SP4 vector as a template and oligonucleotides of SEQ ID NOS: 16 and 17 as primers to amplify the vector from which PR4 was excluded. P11 promoter (SEQ ID NO: 18) was synthesized (Macrogen, Korea). The amplified product and the P11 promoter were ligated by an infusion cloning method, and introduced into *E. coli* to clone a pMT54-P11-IL10-SP4 vector.

3. Transformation and Expression of IL-10 Protein (1) Expression of IL-10 Protein by pMT54-PR4-IL10-SP4 Vector The pMT54-PR4-IL10-SP4 vector and the pMT54-P11-IL10-SP4 vector were transformed into three different kinds of lactic acid bacteria, respectively. The three different kinds of lactic acid bacteria were *Lactobacillus paracasei* KCTC 13422BP, *Lactobacillus plantarum* KCTC 13421BP, and *Lactobacillus brevis* KCTC 13423BP, all separated from kimchi. These strains are also called LMT1-21, LMT1-9, and LMT1-46, respectively.

Each of the strains was cultured in 50 mL of MRS medium (Difco Co., USA) until $OD_{600}$ reached 0.5, and then centrifuged at 4° C. and 7,000 rpm for 10 minutes. Cell pellets were washed twice with 25 mL of ice-cold EPS (EPS: 1 mM $K_2HPO_4$, 1 mM $KH_2PO_4$, pH 7.4, 1 m $MgCl_2$, and 0.5 M sucrose).

After washing, cells were re-suspended in 1 mL of ice-cold EPS, and competent cells to be used in electroporation were prepared, and stored in a deep freezer at −80° C. 40 µl of competent cells and each 1 µl of vector DNA (1 µg/µl) were put in a cuvette and left on ice for 5 minutes. Electric field pulse was applied thereto under conditions of 25 µF, 8 kV/cm, 400 ohms, and the cells were immediately added to 1 mL of MRS liquid medium, followed by incubation at 37° C. for 1 hour. Thereafter, the incubated cells were spread on MRS medium containing 10 µg/ml of chloramphenicol, followed by incubation at 37° C. for 48 hours.

Figure 3:
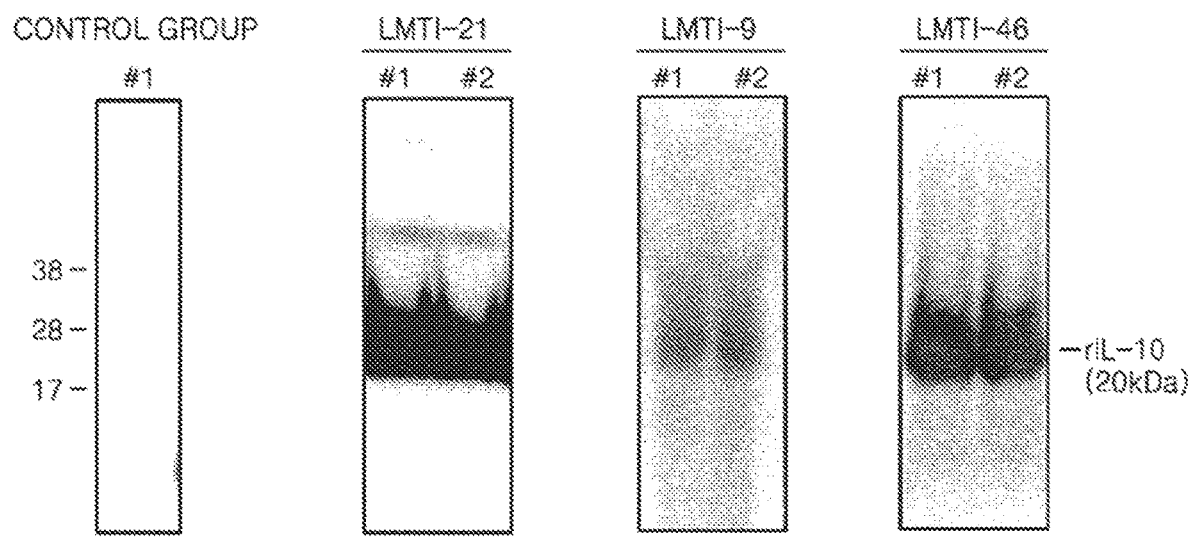
FIG. 3 shows results of examining extracellular expression after transformation of three kinds of lactic acid bacteria with the pMT54-PR4-IL10-SP4 vector.

FIG. 3 shows results of examining extracellular expression after transformation of the three kinds of lactic acid bacteria with the pMT54-PR4-IL10-SP4 vector. In FIG. 3, as a vector of a control group, pMT54-P11-IL10-USP45 was used instead of pMT54-PR4-IL10-SP4.

As shown in FIG. 3, the pMT54-PR4-IL10-SP4 vector showed extracellular expression of IL-10 protein in the three lactic acid bacteria, but the control group showed no expression. These results indicate that the PR4 promoter operated to express the gene and the SP4 signal peptide exerted extracellular secretion of the expressed protein.

(2) Expression at mRNA Level: Examination of Promoter Strength

Each of the pMT54-PR4-IL10-SP4 vector and the pMT54-P11-IL10-SP4 vector was transformed into *Lactobacillus paracasei* KCTC 13422BP (LMT1-21) lactic acid bacterium in the same manner as in (1).

The strain introduced with each of the vector was subjected to stationary culture in MRS medium at 37° C. for 16 hours. 1 ml of the culture was centrifuged at 7,000 rpm for 5 minutes, and then a supernatant was discarded, and a cell pellet was obtained. mRNA was extracted therefrom using an RNA prep kit (Macherey-nagel, cat. no 740955.50) in accordance with the manufacturer's protocol. 100 ng of mRNA was used as a template to synthesize cDNA. cDNA synthesis was performed using a Roketscript cycle RT premix of Bioneer. The synthesized cDNA was used as a template and oligonucleotides of SEQ ID NO: 20 and SEQ ID NO: 21 were used as primers to perform real-time (RT) PCR. RT-PCR was performed using a SYBR premix (takara, RR820B) in accordance with the manufacturer's protocol.

Figure 5:
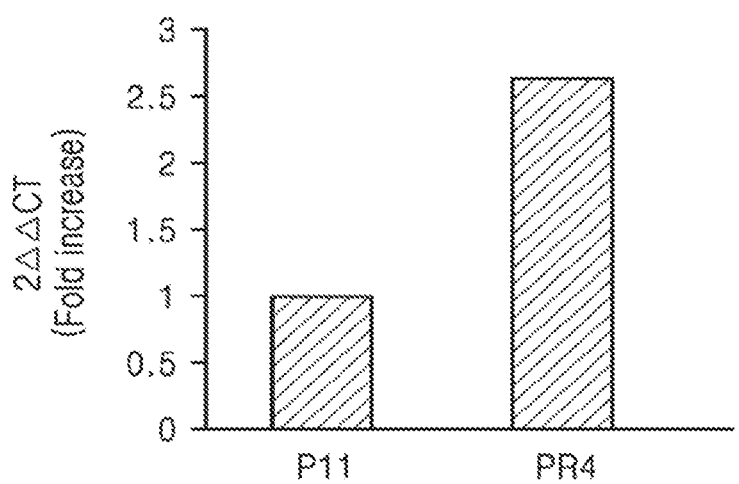
FIG. 5 shows results of measuring IL-10 mRNA levels from pMT54-P11-IL10-SP4 and pMT54-PR4-IL10-SP4 vectors for comparison of promoter strength.

FIG. 5 shows result of RT-PCR which was performed by using cDNA derived from transformed cells as a template.

As shown in FIG. 5, as compared with the *L. paracasei* KCTC13422BP transformed with the pMT54-P11-IL10-SP4 vector, i.e., the control vector, the strain transformed with the pMT54-PR4-IL10-SP4 vector showed remarkably high IL-10 mRNA level. These results indicate that the PR4 promoter strongly operates transcription, as compared with the P11 promoter. In FIG. 5, "2ΔΔCT" on Y axis represents an increase of the transcription level relative to that of the control group in the results of analyzing relative transcription levels.

(3) Expression at Protein Level: Examination of Signal Peptide Strength

Each of the pMT54-PR4-IL10-SP4 vector and the pMT54-PR4-IL10-USP45 vector was transformed into *Lactobacillus paracasei* KCTC 13422BP (LMT1-21) lactic acid bacterium in the same manner as in (1).

The strain introduced with each of the vector was subjected to stationary culture in MRS medium at 37° C. for 16 hours. The culture was seeded in MRS liquid medium at 3 (v/v) %, and then subjected to stationary culture at the same temperature for 8 hours. 1 ml of the culture was centrifuged at 7.000 rpm for 5 minutes, and a supernatant was obtained. 100 μl of trichloroacetic acid was added to 1 ml of the supernatant, which was left at 4° C. for 1 hour to concentrate components of the culture. The resultant was centrifuged at 4° C. and 13,000 rpm for 10 minutes, and a pellet was washed with 1 ml of cold acetone once, dried at room temperature for 10 minutes, and eluted with 100 μl of Tris-HCl buffer (pH 8.8).

A 4× loading buffer (Thermo) and a 10× reducing agent (Thermo) were added to the eluate, followed by electrophoresis on SDS-PAGE gel. This gel was transferred onto a nitrocellulose membrane using a Trans blot semi-dry cell (bio-rad), followed by Western blotting. In detail, the membrane was blocked with a TBST buffer containing 1% skim milk for 1 hour, and reacted with anti-HA antibody (santa cruz) at room temperature for 2 hours. The membrane was washed with TBST for 5 minutes three times, and detected using an ECL. In the pMT54-PR4-IL10-SP4 vector, HA gene was operably linked to IL-10 gene at the 3'-terminus thereof, and thus the HA-tagged gene was expressed.

Figure 6:
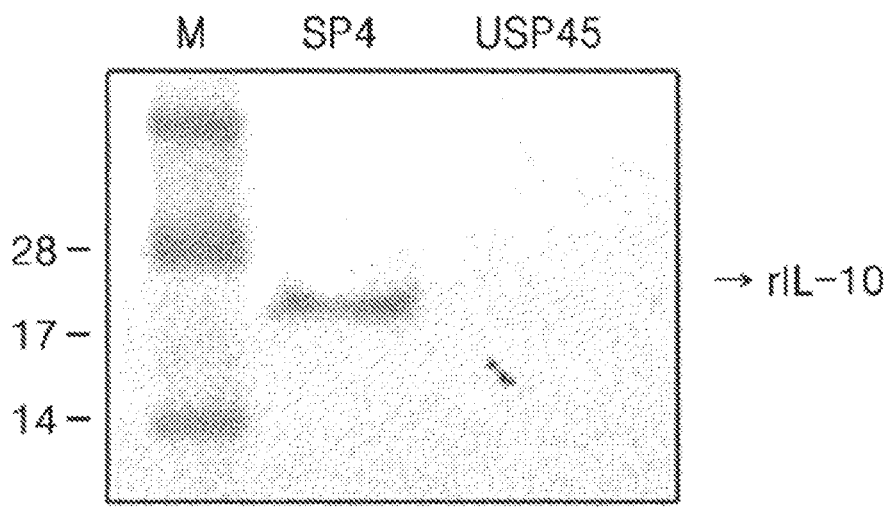
FIG. 6 shows results of measuring quantities of IL-10 secreted from LMT1-21 transformed with pMT54-PR4-IL10-SP4 or pMT54-PR4-IL10-USP45 for comparison of signal peptide strength.

FIG. 6 shows comparison of signal peptide strength by examining quantity of IL-10 secreted from LMT1-21 which was transformed with each of pMT54-PR4-IL10-SP4 and pMT54-PR4-IL10-USP45. As shown in FIG. 6, a larger amount of the expressed protein was secreted by SP4 signal peptide than USP45 signal peptide.

Example 2: Expression of Amylase Gene Using PR4 Promoter and SP4 Sequence

A pMT54-PR4-amylase-SP4 vector was constructed in the same manner as in 2 and 3 of Example 1, except that alpha-amylase gene (SEQ ID NO: 19) instead of IL-10 gene and primers F/R(SEQ ID NOS: 22 and 23) were used, and this vector was transformed into a lactic acid bacterium *L. paracasei* LMT1-21 to examine extracellular expression of alpha-amylase. Amplification of the alpha-amylase gene was performed using genomic DNA of *Lactobacillus* amylovorus (KCTC3597).

Amylase activity of the transformed LMT1-21 strain was examined by an iodine test. First, the LMT1-21 strain introduced with the pMT54-PR4-amylase-SP4 vector was subjected to stationary culture in MRS liquid medium at 37° C. for 12 hours. Thereafter, the culture was applied in small dots to an MRS plate containing 0.5% soluble starch and 10 mg/l of chloramphenicol, and subjected to stationary culture at 37° C. for 12 hours to allow amylase to sufficiently degrade starch. Thereafter, a Lugol's iodine solution (iodine/potassium iodide solution) was evenly applied onto the MRS plate to allow reaction with undegraded starch. As the amylase activity is lower, the amount of remaining starch is larger, and as a result, a strong iodine-starch reaction occurs to show a purple color. On the contrary, as the amylase activity is higher, the amount of starch remaining around cells is smaller, and as a result, a transparent circle is formed.

Figure 4:
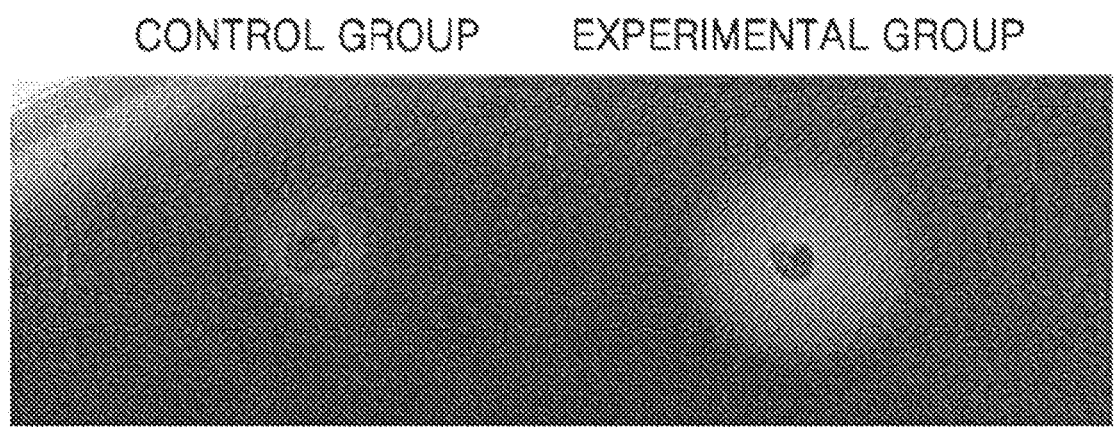
FIG. 4 shows results of examining extracellular expression after transformation of an LMT1-21 strain with a pMT54-PR4-amylase-SP4 vector.

FIG. 4 shows results of examining extracellular expression after transformation of an LMT1-21 strain with pMT54-PR4-amylase-SP4 vector. In FIG. 4, a vector of a control group is the same as the pMT54-PR4-amylase-SP4 vector, except that P11 promoter was used instead of PR4, and USP45 was used instead of SP4.

As shown in FIG. 4, the experimental group using the pMT54-PR4-amylase-SP4 vector showed formation of a large transparent circle due to extracellular expression of alpha-amylase in LMT1-21 strain whereas the control group showed formation of a small transparent circle due to no expression of alpha-amylase. These results indicate that PR4 operated to express amylase gene and extracellular secretion was increased by SP4.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A polypeptide comprising from the N-terminus, a first polypeptide of isolated signal polypeptide having the amino acid sequence of SEQ ID NO:2, and a second polypeptide of a protein, which is heterologous to the isolated signal polypeptide.

2. A recombinant polynucleotide comprising a polynucleotide encoding the polypeptide of claim 1, which comprises a polynucleotide encoding the first polypeptide and a polynucleotide encoding the second polypeptide.

3. The recombinant polynucleotide of claim 2, wherein the polynucleotide encoding the isolated signal polypeptide is operatively linked to the polynucleotide encoding the second polypeptide.

4. The recombinant polynucleotide of claim 3, further comprising a promoter, wherein the promoter is operably linked to the polynucleotide encoding the first polypeptide.

5. The recombinant polynucleotide of claim 2, further comprising a promoter, wherein the promoter is operably linked to the polynucleotide encoding the first polypeptide.

6. The recombinant polynucleotide of claim 2, which is a vector.

7. A host cell comprising the recombinant polynucleotide of claim 2.

8. A method of producing a protein, comprising culturing the host cell of claim 7 in a medium; and isolating the protein from the culture.

9. The recombinant polynucleotide of claim 3, which is a vector.

10. The recombinant polynucleotide of claim 4, which is a vector.

11. The recombinant polynucleotide of claim 5, which is a vector.

12. A host cell comprising the recombinant polynucleotide of claim 3.

13. A host cell comprising the recombinant polynucleotide of claim 4.

14. A host cell comprising the recombinant polynucleotide of claim 5.

15. A method of producing a protein, comprising culturing the host cell of claim 12 in a medium; and isolating the protein from the culture.

16. A method of producing a protein, comprising culturing the host cell of claim 13 in a medium; and isolating the protein from the culture.

17. A method of producing a protein, comprising culturing the host cell of claim 14 in a medium; and isolating the protein from the culture.

* * * * *